(12) United States Patent
Corcoran et al.

(10) Patent No.: US 7,192,435 B2
(45) Date of Patent: Mar. 20, 2007

(54) SELF CENTERING CLOSURE DEVICE FOR SEPTAL OCCLUSION

(75) Inventors: Michael P. Corcoran, Woodbury, MN (US); Joseph A. Marino, Apple Valley, MN (US)

(73) Assignee: Cardia, Inc., Eagan, MN (US)

( * ) Notice: Subject to any disclaimer, the term of this patent is extended or adjusted under 35 U.S.C. 154(b) by 344 days.

(21) Appl. No.: 10/666,080

(22) Filed: Sep. 18, 2003

(65) Prior Publication Data

US 2005/0065546 A1    Mar. 24, 2005

(51) Int. Cl.
*A61B 17/08* (2006.01)
*A61D 1/00* (2006.01)

(52) U.S. Cl. ...................... 606/213; 606/215

(58) Field of Classification Search ............... 606/191, 606/194, 195, 198, 200, 151–155, 213, 215, 606/220, 232
See application file for complete search history.

(56) References Cited

U.S. PATENT DOCUMENTS

| | | | |
|---|---|---|---|
| 3,874,388 A * | 4/1975 | King et al. ............... 600/232 |
| 4,007,743 A | 2/1977 | Blake |
| 4,917,089 A | 4/1990 | Sideris |
| 5,108,420 A | 4/1992 | Marks |
| 5,171,259 A | 12/1992 | Inoue |
| 5,284,488 A | 2/1994 | Sideris |
| 5,334,137 A | 8/1994 | Freeman |
| 5,334,217 A | 8/1994 | Das |
| 5,382,260 A | 1/1995 | Dormandy, Jr. et al. |
| 5,397,331 A | 3/1995 | Himpens et al. |
| 5,425,744 A | 6/1995 | Fagain et al. |
| 5,433,727 A | 7/1995 | Sideris |
| 5,451,235 A * | 9/1995 | Lock et al. ............... 606/213 |
| 5,578,045 A * | 11/1996 | Das ........................ 606/151 |
| 5,634,936 A | 6/1997 | Linden et al. |
| 5,649,950 A | 7/1997 | Bourne et al. |
| 5,683,411 A * | 11/1997 | Kavteladze et al. ........ 606/200 |
| 5,702,421 A | 12/1997 | Schneidt |
| 5,709,707 A | 1/1998 | Lock et al. |
| 5,725,552 A | 3/1998 | Kotula et al. |
| 5,741,297 A | 4/1998 | Simon |
| 5,836,968 A * | 11/1998 | Simon et al. ............... 606/200 |
| 5,846,261 A * | 12/1998 | Kotula et al. ............. 606/213 |
| 5,904,703 A | 5/1999 | Gilson |
| 5,944,738 A * | 8/1999 | Amplatz et al. ........... 606/213 |
| 6,024,756 A | 2/2000 | Huebsch et al. |
| 6,174,322 B1 * | 1/2001 | Schneidt .................. 606/213 |
| 6,206,907 B1 * | 3/2001 | Marino et al. ............. 606/215 |
| 6,221,092 B1 * | 4/2001 | Koike et al. .............. 606/213 |
| 6,267,776 B1 * | 7/2001 | O'Connell ................ 606/200 |

(Continued)

FOREIGN PATENT DOCUMENTS

DE        233 303 A1    2/1986

(Continued)

*Primary Examiner*—Michael J. Hayes
*Assistant Examiner*—Michael G. Mendoza
(74) *Attorney, Agent, or Firm*—Kinney & Lange, P.A.

(57) ABSTRACT

The present invention provides an occluder with a plurality of flexible rings that comprise a self centering mechanism to keep the occluder properly centered in a defect. The self centering mechanism is located between the left and right sides of the occluder. Because the occluder remains properly centered, the chance that portions of the aperture will be exposed is reduced and the effectiveness of the occluder is increased.

39 Claims, 6 Drawing Sheets

U.S. PATENT DOCUMENTS

| | | |
|---|---|---|
| 6,379,368 B1 | 4/2002 | Corcoran et al. |
| 6,402,771 B1 * | 6/2002 | Palmer et al. .............. 606/200 |
| 6,485,496 B1 * | 11/2002 | Suyker et al. .............. 606/153 |
| 6,551,303 B1 * | 4/2003 | Van Tassel et al. .......... 604/508 |
| 2002/0111647 A1 * | 8/2002 | Khairkhahan et al. ...... 606/200 |
| 2003/0045898 A1 * | 3/2003 | Harrison et al. ............. 606/200 |

FOREIGN PATENT DOCUMENTS

| | | |
|---|---|---|
| DE | 4222291 | 1/1994 |
| EP | 0 362 113 A1 | 4/1990 |
| EP | 0 541 063 A2 | 5/1993 |
| EP | 0 541 063 A3 | 5/1993 |
| EP | 0 541 063 B1 | 9/1998 |
| GB | 2 269 321 A | 2/1994 |

* cited by examiner

SELF CENTERING CLOSURE DEVICE FOR SEPTAL OCCLUSION

BACKGROUND OF THE INVENTION

This invention relates to an occlusion device for the closure of physical apertures, such as vascular or septal apertures. More specifically, this invention relates to an occlusion device for the heart that centers itself in the defect to ensure that the defect is properly sealed.

The heart is generally comprised of four chambers: the left and right atrium, and the left and right ventricle. Separating the left and right sides of the heart are two walls, or septa. The wall between the two atria is the interatrial septum and the wall between the two ventricles is the interventricular septum. There are several defects which can affect the septa of both children and adults, including patent ductus arteriosus, patent foramen ovale, atrial septal defects (ASDs), and ventricular septal defects (VSDs). Although the causes and physical aspects of these defects vary by type, each of these defects is generally an aperture, flap, or hole, in the septum which allows blood to shunt between chambers in the heart where there is no blood flow in a normal, healthy heart. This abnormal shunt can cause a variety of health problems.

Normally, permanently repairing certain cardiac defects in adults and children requires open heart surgery, which is a risky, painful, and expensive procedure. Surgery for closure of a heart defect is major heart surgery, which requires the patient to undergo general anesthesia and opening of the chest cavity. The patient must spend several days in the hospital and thereafter may take several weeks to be able to return to normal levels of activity.

To avoid the risks and discomfort associated with open heart surgery, modern occlusion devices have been developed that are small, implantable devices capable of being delivered to the heart through a catheter. These devices effectively seal the defect but do not require surgery. Rather than surgery, a catheter inserted into a major blood vessel allows an occlusion device to be deployed at the defect once the device has been moved through the catheter to the treatment site. This procedure is performed in a cardiac cathlab and avoids the risks and pain associated with open heart surgery.

Modern occlusion devices can repair a wide range of cardiac defects, including patent foramen ovale, patent ductus arteriosus, atrial septal defects, ventricular septal defects, and may occlude other cardiac and non-cardiac apertures. One form of an occlusion device generally has a lower or left side, an upper or right side, and a center section. Once the occluder is deployed, the occluder's center section extends through the center of the defect. The left and right sides occlude the aperture on the respective sides of the patient's septum.

As mentioned, several types of septal defects exist. In addition, the size of defects varies from patient to patient. Some defects are larger than others. If the aperture is large, the center section of the occluder must remain in the center of the defect so that the left and right sides of the occluder occlude the entire aperture. If the center section moves or is not properly centered, the right and left sides follow the center and portions of the aperture may no longer be covered and thus, may be exposed. If portions of the aperture are exposed, blood may continue to shunt through the defect lessening the effectiveness of the occluder. Consequently, there is a need in the art for an occlusion device which has a centering system to keep the device properly centered.

This invention provides an occluder with a self centering system comprising a plurality of elastic rings that keeps the occluder properly centered in the defect. The self centering system allows the center of the occluder to remain properly positioned within the defect so that the left and right sides cover the entire aperture. Because the occluder remains properly positioned, the chance of blood shunting through the aperture is reduced and the effectiveness of the occluder is increased.

BRIEF SUMMARY OF THE INVENTION

The present invention provides an occluder with a plurality of flexible rings that comprise a self centering mechanism system to keep the occluder properly centered in a defect. The self centering mechanism is located between the left and right sides of the occluder. Because the occluder remains properly centered, the chance that portions of the aperture will be exposed is reduced and the effectiveness of the occluder is increased.

DETAILED DESCRIPTION

Figure 1A:
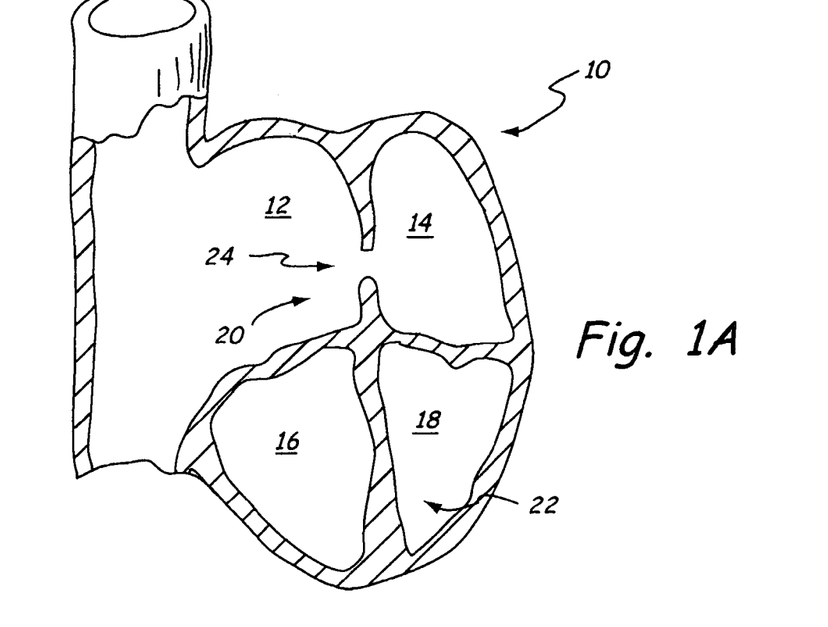
FIG. 1A is a diagram of the heart having a septal defect.

Visible in FIG. 1A is a diagrammatic view of a human heart 10. Visible in FIG. 1A is the right atrium 12, the left atrium 14, the right ventricle 16, the left ventricle 18. The right atrium 12 is separated from the left atrium 14 by a atrial septal wall 20. The right ventricle 16 is separated from the left ventricle 18 by a ventricular septal wall 22. Also visible in FIG. 1A is an atrial septal defect 24 located in the atrial septal wall 20, between the right atrium 12 and left atrium 14 of the heart 10. An atrial septal defect 24 is one example of a cardiac defect that may be occluded using an occlusion device.

Figure 1B:
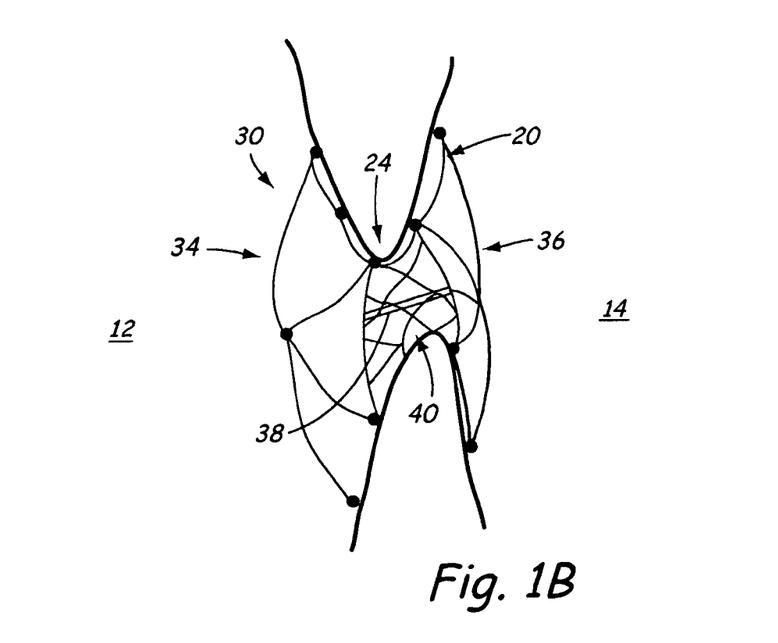
FIG. 1B is a self centering occlusion device in place within a heart having a septal defect.

FIG. 1B is a side view of a self centering closure device 30 for septal occlusion in place in a defect. Shown in FIG. 1B is a more detailed view of the septal wall 20 and the defect 24, shown between the right atrium 12 and the left atrium 14. Also shown is an occlusion device 30. As viewed in FIG. 1B, the occlusion device 30 comprises a right or upper side 34, a left or lower side 36, a center post 38, and a self centering mechanism 40. The right and left sides 34, 36 are so named because they sit in the right and left sides of the patient's heart, respectively. The occlusion device 30 may be inserted into the septal defect 24 via catheter.

For the device 30 to effectively occlude the defect 24, the upper 34 and lower 36 sides must cover the defect 24 entirely. The center post 38 should therefore be located approximately in the center of the defect 24. If the center post 38 shifts in the defect, the upper or lower sides 34, 36 may shift as well which may allow blood to flow through the defect 24. If blood flows through the defect 24, the effectiveness of the occlusion device 30 is decreased. The self centering mechanism 40 helps to keep the center post 38 centered in the defect 24. If the center post 38 is centered in the defect 24, the upper and lower sides 34, 36 remain properly positioned and the chance of blood flowing through the defect 24 is reduced.

The self centering mechanism 40 comprises a honeycomb like structure that is flexible and easily collapsible. However, the design of the self centering mechanism 40 allows the mechanism 40 to expand and to uniformly occlude the space between the center post 38 and the perimeter of the defect 24. By uniformly filling the defect 24, the self centering mechanism 40 can keep the center post 38 in the center of the defect 24. Because the center post 38 remains centered, the upper and lower sides 34, 36 of the device 30 remain properly positioned. The design and function of the self centering mechanism are described in greater detail in FIGS. 4 and 5.

Figure 2:
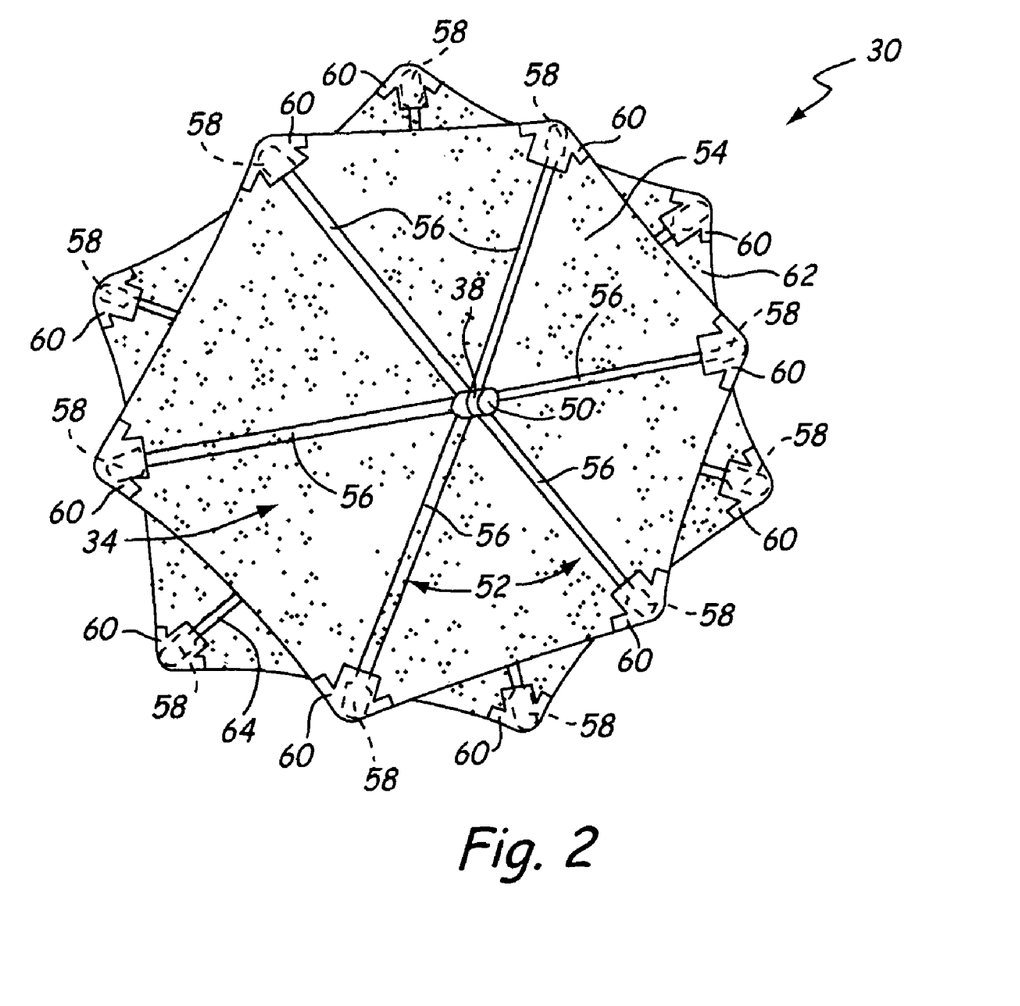
FIG. 2 is a top perspective view of the right or upper side of a self centering occlusion device.

FIG. 2 is a top perspective view of an occlusion device 30. The occlusion device 30 comprises a center post 38 having a grasping knob 50, an upper set of arms 52, and an upper sheet 54. The upper set of arms 52 comprises six wire arms 56 which terminate in atraumatic tips 58. The atraumatic tips 58 are covered by reinforcement patches 60. Also visible in FIG. 2 is a bottom sheet 62 and wire arms 64, which likewise terminate in atraumatic tips 58 covered by patches 60.

Figure 3:
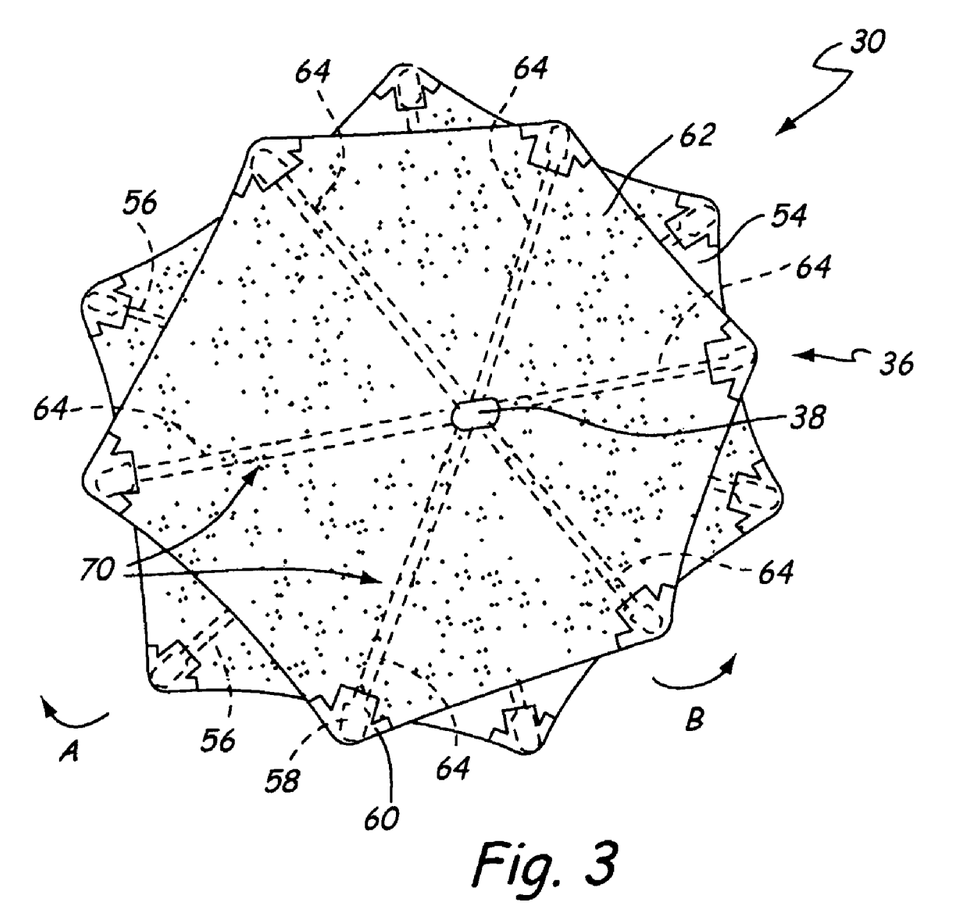
FIG. 3 is a bottom perspective view of the left or lower side of a self centering occlusion device.

FIG. 3 is a bottom perspective view of the occlusion device 30. Shown in FIG. 2 is the center post 38, bottom sheet 62 and lower set of arms 70. The lower set of arms 70 likewise comprises six wire arms 64 which terminate in atraumatic tips 58 covered by reinforcement patches 60. Also shown in FIG. 3 is the upper sheet 54, portions of the wire arms 56 and the atraumatic tips 58 covered by reinforcement patches 60.

The upper and lower set of arms 52, 70 are connected to the center post 38 using any suitable method, including welding, soldering, or adhesives. One method of connecting upper and lower set of arms 52, 70 to the center post 38 is to provide the center post 38 with drill holes through which the upper and lower set of arms 52, 70 extend. To hold the set of arms 52, 70 more securely, the set of arms 52, 70 may additionally be welded, soldered, or otherwise attached to the center post 38 in a more permanent manner.

When connected to the center post 38 using holes drilled through the center post 38, the set of arms 52, 70 may be formed of three wires. The three wires create the six arms 56, 64 because each wire forms two arms when the wire passes through the center post 38. The atraumatic tips 58 are located at the distal end of each arm 56, 64 and serve to minimize damage to the surrounding tissue. Though not shown, the center post 38 may comprise an articulation to allow the device 30 to conform to a wider variety of defects.

Unlike the upper set of arms 52, which is located on an outer side of the upper sheet 54, the lower set of arms 70 is located on an inner side of the lower sheet 62. However, the device 30 is not so limited, and the set of arms 52, 70 may be located on the outer side of the sheets 54, 62, on the inner side of the sheets 54, 62, or any combination thereof.

The sheets 54, 62 are connected to the occlusion device 30 at the center post and at the upper and lower set of arms 52, 70. The sheets 54, 62 may be connected to the set of arms 52, 70 using any suitable method. One method of attaching the sheets 54, 62 to the set of arms 52, 70 is to suture the sheets 54, 62 to the set of arms 52, 70 along the length of the arms 56, 64. Alternatively, the sheets 54,62 maybe sewn to device 30 at the atraumatic tips 58. To do so, the atraumatic tips 58 may be provided with drilled holes through which sutures can pass to sew the sheets 54, 62 to the tips 58.

The reinforcement patches 60 are configured to fit over the atraumatic tips 58. The reinforcement patches 60 are placed at the end of the atraumatic tips 58 and are folded over the tips 58 so that the tips 58 are covered on both their top and bottom sides. The patches 60 may be secured to the sheets 54, 62 using any suitable method, including sutures, heat treatment, or laminating.

The reinforcement patches 60 serve to reinforce the foam sheets 54, 62 near the ends of the wire arms 56, 64. This reinforcement helps strengthen the sheets 54, 62 at the locations they are likely to tear or wear. The reinforcement patches 60 also act as a cushion between the metal tips 58 of the occlusion device 30 and the tissue surrounding the defect. The patches 60 provide extra protection of the tissue from the pressure that the device 30 exerts on the tissue at the atraumatic tips 58.

The occlusion device 30 is configured to be deployed through a catheter, and the grasping knob 50 on the center post 38 is configured to allow the occlusion device 30 to be grasped by a forceps as it is guided through the catheter. More specifically, the occlusion device 30 is constructed so that the upper and lower set of arms 52, 70 are easily collapsible about the center post 38. Due to this construction, the occlusion device 30 can be folded so that the upper set of arms 52 is folded upwards in the axial direction A and the lower set of arms 70 is folded downwards in the opposite axial direction B. The upper and lower sheets 54, 62 attached to the upper and lower set of arms 52, 70 are also flexible, and can likewise collapse as the upper and lower devices 52, 70 are folded.

The occlusion device 30 is preferably made from biocompatible materials with the desired properties. More specifically, the wire set of arms 52, 70 are preferably formed of a material that is capable of shape memory. One such suitable material is a nickel-titanium alloy, commonly called Nitinol. Nitinol is preferably used because it is commercially available, very elastic, non-corrosive, and has a fatigue life greater than that of stainless steel. Similarly, the center post 12 maybe formed of platinum iridium, the atraumatic tips 58 maybe formed of titanium, and any sutures may be formed of polypropylene, all of which are bio-compatible.

The sheets 54, 62 are comprised of a medical grade polymer in the form of film, foam, gel, or a combination thereof One suitable material is DACRON®. Preferably, a high density polyvinyl alcohol (PVA) foam is used, such as that offered under the trademark IVALON®. To minimize the chance of the occlusion device 30 causing a blood clot, the foam sheets 54, 62 may be treated with a thrombosis inhibiting material. One such suitable material is heparin.

In some instances, it may be desirable to form the sheets 54, 62 so that they are not both the same size. For instance, one sheet and its associated set of arms can be made smaller than the corresponding sheet and its associated set of arms. This is particularly useful in situations where the occlusion device 30 is to be placed at a location in the heart which is close to other nearby cardiac structures. Making the sheets 54, 62 different sizes may assist in providing optimal occlusion of a defect, without affecting other structures of the heart which may be nearby.

To ensure the occlusion device 30 is effective at closing a septal defect even after it has been passed through a catheter, the wire arms 56, 64 are preferably subjected to a precise pre-shaping to give them a "shape memory." The pre-shaping can be done either by machining, heat treatment, or both. The shape memory helps to hold the strands together and can be used to add pre-tension to the wire arms 56, 64 so that they remember their shape even after the strong deformation that occurs when the occlusion device 30 is passed through the catheter.

In the past, occlusion devices have suffered from fatigue failures, such as cracks or breaks, due to the extreme environment the human heart poses. To avoid fatigue failure of the set of arms 52, 70, one embodiment of the present invention relies on making the wire set of arms 52, 70 of stranded wire or cables. The stranded wire or cable improves the fatigue life of the set of arms 52, 70 without increasing their size or decreasing their strength. The atraumatic tips 58 cap the wire arms 56, 64 and can serve to prevent potential unraveling of the strands in addition to preventing damage to surrounding tissue.

Another feature of the invention is the number of arms 56, 64 provided on the upper and lower set of arms 52, 70. The occlusion device 30 is provided with an increased number of arms 56, 64, but the stiffness and tension of each arm 56, 64 is decreased. One method of decreasing the stiffness and tension of each arm is to decrease the diameter of the wire, stranded wires, or cable that form each arm 56, 64. When formed of stranded wire or cables, the individual strands which make up the stranded wire or cable may range in diameter from about 0.001 inches to about 0.15 inches. The overall diameters of the arms 56, 64, even when formed of stranded wire, may range from as small as about 0.003 inches to about 0.050 inches.

Each arm 56, 64 maybe equally spaced from an adjacent arm. In the six arm device 30, each arm 56, 64 is located 60° from the adjacent arm. In addition, to assist in maximizing the occlusion ability of the six arm device 30, the upper sheet 54 may be offset from the bottom sheet 62. The amount one sheet is offset from the other may vary based on the desired performance of the device 30. In one embodiment, the upper sheet 54 is offset from the bottom sheet 62 at an angle of about 30°.

Figure 4:
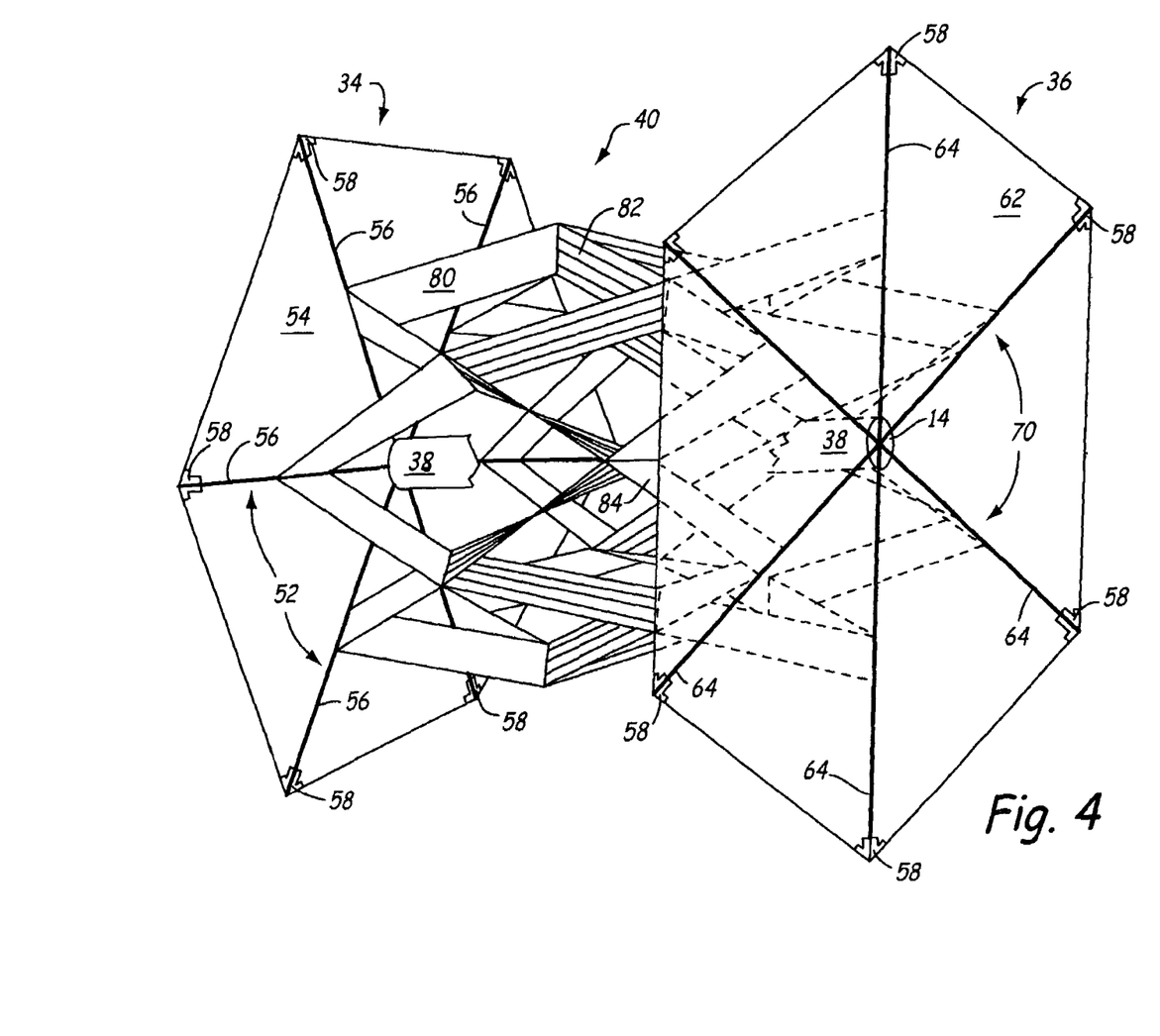
FIG. 4 is a partially exploded perspective side view of an occlusion device having a self centering system that has been pulled apart slightly to reveal the centering system

FIG. 4 is a partially exploded perspective side view of an occlusion device 30 having a self centering mechanism 40. The device 30 has been pulled apart slightly to reveal the centering mechanism 40 and the center post 38 is broken so that the device 30 may be pulled apart. Shown is an upper side 34, the upper set of arms 52 comprised of individual arms 56, end caps 58, and the upper sheet 54, a lower side 36, the lower set of arms 70 comprised of individual arms 64, atraumatic tips 58, the lower sheet 62, and the center post 38, which is broken in this exploded view so the device 30 may be pulled apart and the self centering mechanism 40 may be more easily observed. Also shown are three elastic rings 80, 82, 84 which comprise the self centering mechanism 40. In this example, the rings 80, 82, 84 are constructed of polyvinyl alcohol foam but the material is not so limited. The rings 80, 82, 84 may be constructed of any material that is biocompatible, such as wire, polymer or elastomer. Ideally, however, the material used to create the rings 80, 82, 84 provides some elasticity. Additionally, the rings 80, 82, 84 may be treated with a thrombosis inhibiting material such as heparin.

The self centering mechanism 40 consists of three rings 80, 82, 84. The second ring 82 has been shaded to allow the viewer to easily differentiate between the first, second, and third rings 80, 82, 84. Each ring 80, 82, 84 is connected to the adjacent rings, and the rings adjacent to either the upper side 34 or the lower side 36 are connected to the adjacent side 34, 36. The rings 80, 82, 84 are connected at discrete locations using sutures or another suitable method such as laminating or heating.

The self centering mechanism 40 provides a flexible honeycomb like system that can fill the aperture of the defect and keep the center post 38 in the center of the defect. As mentioned previously, having the center post 38 positioned in the center of the defect keeps the upper and lower sides 34, 36 from shifting and exposing portions of the defect. If portions of the defect are exposed or not covered by the upper and lower sides 34, 36, blood will continue to flow through the defect. The self centering mechanism 40 is flexible and can expand to fill the aperture but will not expand the aperture itself. Thus, the self centering mechanism 40 either expands to fill the diameter of the aperture or, alternatively, compresses if the aperture is small. Another advantage of the self centering mechanism 40 is that it does not add much mass to device 30 and does not interfere with the ability of the device 30 to maintain a low profile when deployed.

As mentioned, the multiple ring design creates a honeycomb like system having a series of cells, or chambers, defined by the rings 80, 82, 84. The cells are visible when the rings 80, 82, 84 are pulled apart. Each cell has four sides which are defined by segments of rings 80, 82, 84 which surround the cells. The cells size and shape varies based on the amount of distance between the upper and lower sides 34, 36 of the device. As the upper and lower sides 34, 36 are pulled apart, the rings 80, 82, 84 experience stretching, which changes the size and shape of the cells.

The honeycomb design allows the self centering mechanism 40 to fill an area that is greater than the physical area of the rings 80, 82, 84 because the cells also occupy space between the rings 80, 82, 84. Thus, the combination of rings 80, 82, 84 and cells, which are defined by the rings 80, 82, 84, can fill a large defect. By filling the defect uniformly on all sides around the center post 38, the center post 38 is kept in the center of the defect. Very little material is used to create the self centering mechanism 40, so there is not much mass in the opening of the defect. If the defect opening is small, the rings do not move apart and thus, the size of the cells is small. If there is limited space, the material used to form the rings 80, 82, 84 and the cells defined by the rings 80, 82, 84 compress. Therefore, the self centering mechanism 40 does not expand the aperture of the defect.

As mentioned, the material used to form the rings 80, 82, 84 should be flexible and, ideally, somewhat elastic so the rings 80, 82, 84 may expand but also compress easily. Elasticity is helpful in allowing the ring structure to easily expand and compress. Thus, elasticity may be particularly useful when the device 30 is loaded into a catheter. Elasticity also allows the rings 80, 82, 84 to resume their shape if stretched.

Figure 5A:
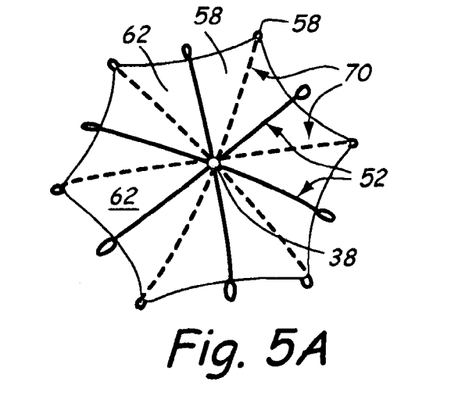
FIGS. 5A–5E are a series of diagrams showing how the self centering system is assembled.

FIGS. 5A–5E are a series of diagrams showing how the self centering system is assembled. Shown in FIG. 5A is a lower sheet 62, lower sets of arms 70, upper set of arms 52, atraumatic tips 58, and the center post 38. The upper sheet 54 (visible in FIG. 2) is not yet attached. Thus, only the frame of the upper side 34 is visible.

Figure 5B:
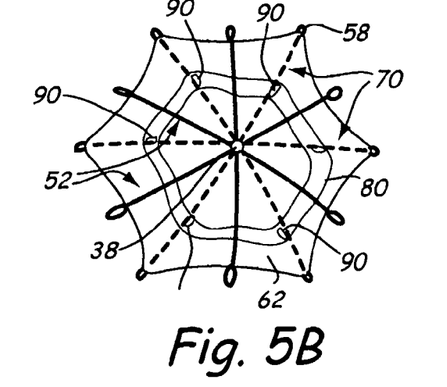
Figure 5C:
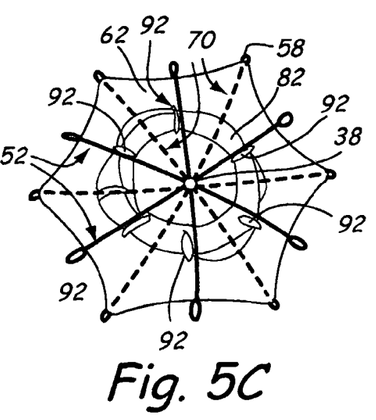
Figure 5D:
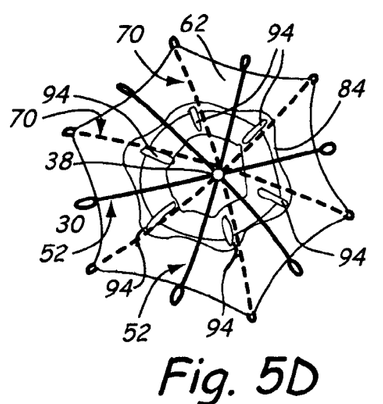
Figure 5E:
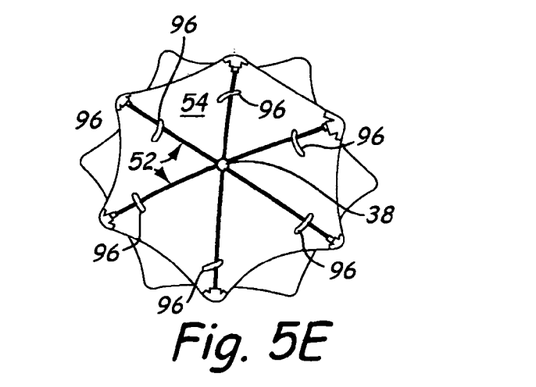

In FIG. 5B, the first ring 80 is added between the upper set of arms 52 and the lower sheet 62. The first ring 80 is sutured 90 to the lower sheet 62 where the lower set of arms 70 is located. Thus, the sutures 90 occur in six locations. In FIG. 5C, the second ring 82 is added between the upper set of arms 52 and the first ring 80. The second ring 82 is sutured 92 to the first ring 80 at six locations. In FIG. 5D, the third ring 84 is added between the upper set of arms 52 and the second ring 82. The third ring 84 is sutured 94 to the second ring 82 at six locations. In FIG. 5E, the top sheet 54 is added between the upper set of arms 52 and the third ring 86. The upper sheet 18 is sutured 96 at six locations along the upper arms 52 to the third ring 48.

As visible in FIGS. 5B through 5D, the suture 92, 94, 96 sites are alternated with each new layer which provides the honeycomb-like design of the self centering mechanism 40. The honeycomb design provides the device 30 with a flexible self centering mechanism 40 that can be flattened or expanded axially as necessary to fill the aperture by creating the ring 80, 82, 84 and cell configuration discussed previously.

As mentioned previously, the self centering mechanism 40 fills the aperture and thus, positions the occlusion device 30 so that the center post 38 is in the center of the aperture. If the center post 38 is in the center of the aperture, the upper and lower sides 34, 36 of the device 30 are more likely to effectively occlude the defect to reduce blood flow across the defect.

The honeycomb design also allows the device 30 to be folded axially, with the sides 34, 36 facing away from one another so that the device 30 may be loaded into a catheter. The diameter of the rings 80, 82, 84 may be slightly larger than the diameter of the sutures 90, 92, 94, 96 to provide extra ring material. Extra ring material 80, 82, 84 provides additional aperture filling capacity and also allows the device 30 to be folded to fit into a catheter 100.

Figure 6:
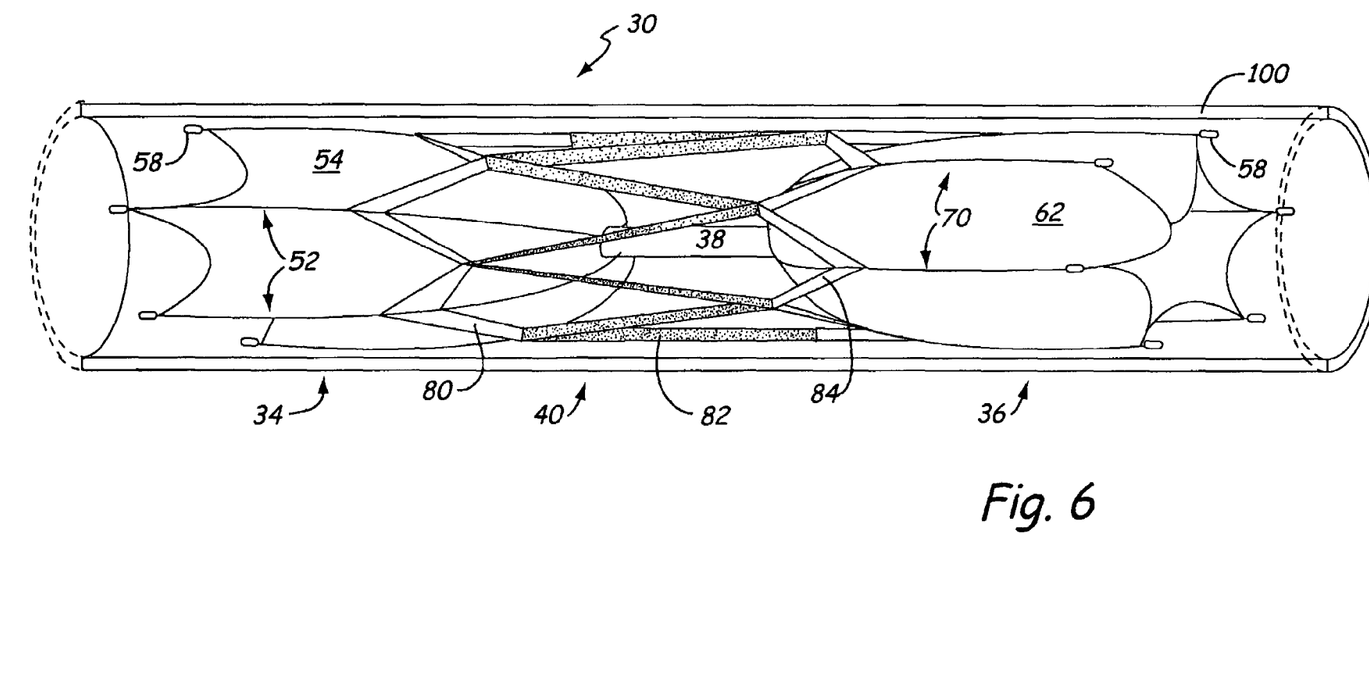
FIG. 6 is a side view of an occlusion device having a self centering system that has been loaded into a catheter.

FIG. 6 is a side view of an occlusion device having a self centering system that has been loaded into a catheter. Shown is the device 30 loaded inside a catheter 100. Visible in FIG. 6 is the upper side 34, upper set of arms 52, the upper sheet 54, the lower side 36, lower set of arms 70, the lower sheet 62, the center post 38, atraumatic tips 58, the self centering mechanism 40, the first ring 80, the second ring 82, and the third ring 84. The second ring 82 has been shaded to allow the viewer to easily differentiate between the first, second, and third rings 80, 82, 84.

As mentioned, alternating the attachment sites of the rings 80, 82, 84 forms a honeycomb-like design. The positioning of the attachment sites of the rings 80, 82, 84 allows the self centering mechanism 40 to have a large axial span, which does not interfere with the loading or deployment of the device 30. The axial span of the centering mechanism 40 may be increased by slightly increasing the diameter of the rings 80, 82, 84. Because of the axial span, both the upper and lower sides 34, 36 can fold away from each other and the device 30 maybe loaded easily into the catheter 100. Thus, the configuration of the rings 80, 82, 84, combined with the elasticity of the rings 80, 82, 84 allows the device 30 to be folded axially, with the sides 34, 36 facing away from one another and loaded into a catheter. If the material used to construct the rings 80, 82, 84 is stretchy, the rings 80, 82, 84 readily resume their shape after the device 30 exits the catheter 100.

Although the present invention has been described with reference to preferred embodiments, workers skilled in the art will recognize that changes may be made in form and detail without departing from the spirit and scope of the invention.

The invention claimed is:

1. An occlusion device comprising:
 a left side having a first set of arms;
 a right side having a second set of arms, wherein the right side is spaced from and connected to the left side; and
 a self centering mechanism which is laterally expandable to fill a defect, the mechanism comprising at least three rings located between the left and right sides wherein:
  a first ring is connected to the left side;
  a second ring is connected to the first ring; and
  a third ring is connected to the second ring and to the right side.

2. The occlusion device of claim 1 wherein heat laminating is used to connect the first ring to the left side, the second ring to the first ring, the second ring to the third ring, and the third ring to the right side at laminated locations.

3. The occlusion device of claim 2 wherein the laminated locations connecting the first ring to the left side are offset from the laminated locations connecting the second ring to the first ring, the laminated locations connecting the second ring to the third ring are offset from the laminated locations connecting the first ring to the second ring, and the laminated locations connecting the third ring to the right side are offset from the laminated locations connecting the third ring to the second ring.

4. The occlusion device of claim 1 wherein the rings comprise a non-thrombogenic material.

5. The occlusion device of claim 1 wherein the rings comprise biocompatable wire.

6. An occlusion device comprising:
 a left side;
 a right side connected to the left side; and
 a self centering mechanism comprising at least three rings located between the left and right sides wherein:
  a first ring is connected to the left side;
  a second ring is connected to the first ring;
  a third ring is connected to the second ring and to the right side, and;
 wherein sutures are used to connect the first ring to the left side, the second ring to the first ring, the second ring to the third ring, and the third ring to the right side at suture locations.

7. The occlusion device of claim 6 wherein the suture locations connecting the first ring to the left side are offset from the sutures connecting the second ring to the first ring, the sutures connecting the second ring to the third ring are offset from the sutures connecting the first ring to the second ring, and the sutures connecting the third ring to the right side are offset from the sutures connecting the third ring to the second ring.

8. An occlusion device comprising:
 a left side;
 a right side connected to the left side; and
 a self centering mechanism which is laterally expandable to fill a defect, the mechanism comprising at least three rings located between the left and right sides wherein:
  a first ring is connected to the left side;
  a second ring is connected to the first ring;
  a third ring is connected to the second ring and to the right side, and;
 wherein the rings comprise polyvinyl alcohol foam.

9. An occlusion device comprising:
 a center post;
 first and second sets of arms connected to the center post, the first and second set of arms comprising at least five arms;
 first and second sheets attached to the first and second sets of arms respectively; and
 a self centering mechanism which is laterally expandable to fill a defect, the mechanism comprising a plurality of flexible rings wherein:
  a first ring is connected to the first set of arms;

a second ring is connected to the first ring;
a third ring is connected to the second ring and to the second set of arms.

10. The occlusion device of claim 9 wherein sutures are used to connect the first ring to a left side of the occlusion device, the second ring to the first ring, the second ring to the third ring, and the third ring to a right side of the occlusion device at suture locations.

11. The occlusion device of claim 10 wherein the suture locations connecting the first ring to the first side are offset from the sutures connecting the second ring to the first ring, the sutures connecting the second ring to the third ring are offset from the sutures connecting the first ring to the second ring, and the sutures connecting the third ring to the second side are offset from the sutures connecting the third ring to the second ring.

12. The occlusion device of claim 9 wherein heat laminating is used to connect the first ring to a left side of the occlusion device, the second ring to the first ring, the second ring to the third ring, and the third ring to a right side of the occlusion device at laminated locations.

13. The occlusion device of claim 12 wherein the laminated locations connecting the first ring to the left side are offset from the laminated locations connecting the second ring to the first ring, the laminated locations connecting the second ring to the third ring are offset from the laminated locations connecting the first ring to the second ring, and the laminated locations connecting the third ring to the right side are offset from the laminated locations connecting the third ring to the second ring.

14. The occlusion device of claim 9 wherein the rings comprise polyvinyl alcohol foam.

15. The occlusion device of claim 9 wherein the rings comprise a non-thrombogenic material.

16. The occlusion device of claim 9 wherein the rings comprise biocompatable wire.

17. A method of manufacturing a self centering mechanism for an occlusion device, the method comprising:
forming a centering mechanism by attaching a first ring to a second ring and attaching the second ring to a third ring;
securing the first ring to a first interior side of the occlusion device;
securing the third ring to a second interior side of the occlusion device; and
wherein sutures are used to connect the first ring to the first interior side of an occlusion device, the second ring to the first ring, the second ring to the third ring, and the third ring to the second interior side at suture locations.

18. The method of manufacture of claim 17 wherein the suture locations connecting the first ring to the first interior side are offset from the sutures connecting the second ring to the first ring, the sutures connecting the second ring to the third ring are offset from the sutures connecting the first ring to the second ring, and the sutures connecting the third ring to the second interior side are offset from the sutures connecting the third ring to the second ring.

19. The method of manufacture of claim 17 wherein the rings comprise a non-thrombogenic material.

20. The method of manufacture of claim 17 wherein the rings comprise biocompatable wire.

21. A method of manufacturing a self centering mechanism for an occlusion device, the method comprising:
forming a centering mechanism by attaching a first ring to a second ring and attaching the second ring to a third ring;
securing the first ring to a first interior side of the occlusion device;
securing the third ring to a second interior side of the occlusion device; and
wherein heat laminating is used to connect the first ring to the first interior side, the second ring to the first ring, the second ring to the third ring, and the third ring to the second interior side at laminated locations.

22. The method of manufacture of claim 21 wherein the laminated locations connecting the first ring to the first interior side are offset from the laminated locations connecting the second ring to the first ring, the laminated locations connecting the second ring to the third ring are offset from the laminated locations connecting the first ring to the second ring, and the laminated locations connecting the third ring to the second interior side are offset from the laminated locations connecting the third ring to the second ring.

23. A method of manufacturing a self centering mechanism for an occlusion device, the method comprising:
forming a centering mechanism by attaching a first ring to a second ring and attaching the second ring to a third ring;
securing the first ring to a first interior side of the occlusion device;
securing the third ring to a second interior side of the occlusion device; and
wherein the rings comprise polyvinyl alcohol foam.

24. An occlusion device comprising:
a center post;
first and second sets of arms connected to the center post, the first and second set of arms comprising at least five arms;
first and second sheets attached to the first and second sets of arms respectively; and
a self centering mechanism comprising a flexible honeycomb structure surrounding the center post and connected between the first and second set of arms.

25. The occlusion device of claim 24 wherein sutures are used to connect the first ring to a left side of the occlusion device, the second ring to the first ring, the second ring to the third ring and the third ring to a right side of the occlusion device at suture locations.

26. The occlusion device of claim 25 wherein the suture locations connecting the first ring to the first side are offset from the sutures connecting the second ring to the first ring, the sutures connecting the second ring to the third ring are offset from the sutures connecting the first ring to the second ring, and the sutures connecting the third ring to the second side are offset from the sutures connecting the third ring to the second ring.

27. The occlusion device of claim 24 wherein heat laminating is used to connect the first ring to a left side of the occlusion device, the second ring to the first ring, the second ring to the third ring and the third ring to a right side of the occlusion device at laminated locations.

28. The occlusion device of claim 27 wherein the laminated locations connecting the first ring to the left side are offset from the laminated locations connecting the second ring to the first ring, the laminated locations connecting the second ring to the third ring are offset from the laminated locations connecting the first ring to the second ring, and the laminated locations connecting the third ring to the right side are offset from the laminated locations connecting the third ring to the second ring.

29. The occlusion device of claim 24 wherein the rings comprise polyvinyl alcohol foam.

30. The occlusion device of claim 24 wherein the rings comprise a non-thrombogenic material.

31. The occlusion device of claim 24 wherein the rings comprise biocompatable wire.

32. An occlusion device comprising:
a left side having a first set of arms;
a right side having a second set of arms;
a center post connecting the left side to the right side and configured to extend through an aperture;
a self centering mechanism located between the left and right sides and surrounding the center post wherein the self centering mechanism laterally expands to fill the aperture radially around the center post; and
wherein the self centering mechanism comprises at least three rings located between the left and right sides wherein:
a first ring is connected to the left side;
a second ring is connected to the first ring;
a third ring is connected to the second ring and to the right side.

33. The occlusion device of claim 32 wherein sutures are used to connect the first ring to the left side, the second ring to the first ring, the second ring to the third ring, and the third ring to the right side at suture locations.

34. The occlusion device of claim 33 wherein the suture locations connecting the first ring to the left side are offset from the sutures connecting the second ring to the first ring, the sutures connecting the second ring to the third ring are offset from the sutures connecting the first ring to the second ring and the sutures connecting the third ring to the right side are offset from the sutures connecting the third ring to the second ring.

35. The occlusion device of claim 32 wherein heat laminating is used to connect the first ring to the left side, the second ring to the first ring, the second ring to the third ring, and the third ring to the right side at laminated locations.

36. The occlusion device of claim 35 wherein the laminated locations connecting the first ring to the left side are offset from the laminated locations connecting the second ring to the first ring, the laminated locations connecting the second ring to the third ring are offset from the laminated locations connecting the first ring to the second ring, and the laminated locations connecting the third ring to the right side are offset from the laminated locations connecting the third ring to the second ring.

37. The occlusion device of claim 32 wherein the rings comprise polyvinyl alcohol foam.

38. The occlusion device of claim 32 wherein the rings comprise a non-thrombogenic material.

39. The occlusion device of claim 32 wherein the rings comprise biocompatable wire.

* * * * *

UNITED STATES PATENT AND TRADEMARK OFFICE
CERTIFICATE OF CORRECTION

PATENT NO. : 7,192,435 B2  Page 1 of 1
APPLICATION NO. : 10/666080
DATED : March 20, 2007
INVENTOR(S) : Michael P. Corcoran et al.

It is certified that error appears in the above-identified patent and that said Letters Patent is hereby corrected as shown below:

Column 3, Line 67, delete "maybe", insert --may be--

Column 4, Line 42, delete "maybe", insert --may be--

Column 4, Line 43, delete "maybe", insert --may be--

Column 5, Line 31, delete "maybe", insert --may be--

Column 7, Line 48, delete "maybe", insert --may be--

Signed and Sealed this

Twenty-sixth Day of June, 2007

JON W. DUDAS
*Director of the United States Patent and Trademark Office*